United States Patent [19]

Letton et al.

[11] Patent Number: 5,306,514

[45] Date of Patent: * Apr. 26, 1994

[54] SOLID, NONDIGESTIBLE, FAT-LIKE COMPOUNDS AND FOOD COMPOSITIONS CONTAINING SAME

[75] Inventors: James C. Letton, Forest Park; Deborah J. Back, Cleves; John R. Baginski, Loveland; Joseph J. Elsen, Cincinnati; Timothy B. Guffey; Jeffrey J. Kester, both of West Chester; David J. Weisgerber, Cincinnati, all of Ohio

[73] Assignee: The Procter & Gamble Company, Cincinnati, Ohio

[ * ] Notice: The portion of the term of this patent subsequent to Aug. 17, 2010 has been disclaimed.

[21] Appl. No.: 81,959

[22] Filed: Jun. 24, 1993

Related U.S. Application Data

[63] Continuation of Ser. No. 751,406, Aug. 28, 1991, abandoned, which is a continuation of Ser. No. 514,794, Apr. 26, 1990, abandoned.

[51] Int. Cl.$^5$ .................................................. A23L 1/00
[52] U.S. Cl. ..................................... 426/531; 426/601; 426/804; 536/119
[58] Field of Search .............. 426/531, 601, 603, 606, 426/607, 611, 612, 804; 536/119

[56] References Cited

U.S. PATENT DOCUMENTS

| | | | |
|---|---|---|---|
| 3,093,481 | 6/1963 | Ecky et al. | 426/118 |
| 3,158,490 | 11/1964 | Baur et al. | 426/612 |
| 3,600,186 | 8/1971 | Mattson et al. | |
| 4,005,195 | 1/1977 | Jandacek. | |
| 4,789,664 | 12/1988 | Seligson et al. | 514/23 |
| 4,797,300 | 1/1989 | Jandacek et al. | 426/549 |
| 4,840,815 | 6/1989 | Meyer et al. | 426/61 |
| 4,940,601 | 7/1991 | Orphanos et al. | 426/601 |
| 5,236,733 | 8/1993 | Zimmerman et al. | 426/611 |

FOREIGN PATENT DOCUMENTS

| | | |
|---|---|---|
| 233856 | 3/1987 | European Pat. Off. . |
| 236288 | 9/1987 | European Pat. Off. . |
| 0290421 | 11/1988 | European Pat. Off. . |
| 311154 | 4/1989 | European Pat. Off. . |
| 227137 | 9/1985 | German Democratic Rep. . |
| 228457 | 10/1985 | German Democratic Rep. . |
| 52-27694 | 7/1977 | Japan . |
| 58-78531 | 5/1983 | Japan . |
| 4926220 | 3/1984 | Japan . |
| 59-143550 | 8/1984 | Japan . |
| 59-156242 | 9/1984 | Japan . |
| 1-252251 | 6/1989 | Japan . |

*Primary Examiner*—Donald E. Czaja
*Assistant Examiner*—Leslie Wong
*Attorney, Agent, or Firm*—Eric W. Guttag; Ronald L. Hemingway; Tara M. Rosnell

[57] ABSTRACT

Fatty acid esters of polyols having at least 4 hydroxyl groups wherein the fatty acid groups consist essentially of: (1) long chain unsaturated fatty acid radicals containing at least 12 carbon atoms or mixtures of said unsaturated radicals with saturated fatty acid radicals containing 2 to 12 carbon atoms, and (2) long chain saturated fatty acid radicals containing at least 20 carbon atoms, wherein the molar ratio of (1):(2) is from 1:15 to 2:1 and wherein at least 4 of the hydroxyl groups of the polyol are esterified. The compounds are useful as nondigestible substitutes for solid fats in foods.

30 Claims, No Drawings

SOLID, NONDIGESTIBLE, FAT-LIKE COMPOUNDS AND FOOD COMPOSITIONS CONTAINING SAME

This is a continuation of application Ser. No. 07/751,406, filed on Aug. 28, 1991, now abandoned, which is a continuation of application Ser. No. 07/514,794, filed on Apr. 26, 1990, now abandoned.

FIELD OF THE INVENTION

The invention pertains to novel, nondigestible, solid fat-like compounds which are particularly useful as additives to liquid edible oils. They can be used in blends with liquid nondigestible oils to control passive oil loss through the anal sphincter when said oils are ingested. They can also be used as non-caloric thickening agents with liquid digestible or nondigestible oils to formulate fluid cooking and salad oils or semi-solid oleaginous products such as shortening and margarines.

BACKGROUND ART

In recent years considerable attention has been focused on the amount of triglyceride fat in the diet from the standpoint of health concerns about obesity and hypercholesterolemia. Numerous patents have been directed to providing materials which have the physical and gustatory characteristics of triglyceride fats, but which are absorbed to a low extent or not at all by the body. These materials are referred to variously as non-caloric fats, pseudofats, nondigestible fats and fat substitutes. Patents pertaining to such materials include U.S. Pat. No. 4,582,927, Fulcher, issued Apr. 15, 1986, (fatty esters of malonic acid); U.S. Pat. No. 4,582,715, Volpenhein, issued Apr. 15, 1986, (alpha acetylated triglycerides); and U.S. Pat. No. 3,579,548, Whyte, issued May 18, 1971, (triglycerides of alpha-branched chain carboxylic acids).

One particular type of compound which has achieved considerable attention as a nondigestible fat is sucrose polyester (i.e., sucrose in which at least four of the eight hydroxyl groups are esterified with a fatty acid). U.S. Pat. No. 3,600,186, Mattson, issued Aug. 17, 1971; U.S. Pat. No. 4,368,213, Hollenbach et al. issued Jan. 11, 1983; and U.S. Pat. No. 4,461,782, Robbins et al. issued Jul. 24, 1984 describe the use of this material as a nondigestible fat in a variety of food compositions.

A problem associated with moderate to high levels of ingestion of liquid nondigestible fats, i.e., those having a melting point below body temperature (about 37° C.), is an undesired passive oil loss effect, which is manifested in leakage of the liquid nondigested fat through the anal sphincter. U.S. Pat. No. 4,005,195, Jandacek, issued Jan. 25, 1977, discloses the combining of higher melting fatty materials such as solid triglycerides and solid sucrose polyesters with the liquid sucrose polyesters in order to avoid the oil loss effect.

U.S. Pat. No. 4,797,300 (Jandacek et al.), issued Jan. 10, 1989 discloses the use of certain solid sucrose polyesters which have high oil binding capacity for liquid sucrose polyesters and liquid triglycerides, when used at levels of about 10% to 25% in said oils. It is disclosed that because of their high oil binding capacity, these solid sucrose polyesters have outstanding utility as agents to control or prevent passive oil loss of liquid nondigestible sucrose polyesters, and they are also useful as non-caloric hardstocks to use with liquid digestible or nondigestible oils in the preparation of semi-solid fat products such as shortenings and margarines. The oil binding agents of the Jandacek et al. '300 patent are solid sucrose polyesters wherein the ester groups consist essentially of a mixture of short chain saturated fatty acid ester radicals ($C_2$–$C_{10}$) and long chain saturated fatty acid radicals ($C_{20}$–$C_{24}$) in a molar ratio of short chain to long chain of from about 3:5 to about 5:3, and wherein the degree of esterification is from about 7 to about 8.

U.S. Pat. 3,158,490 (Baur et al.), issued Nov. 24, 1964 discloses sucrose (and other disaccharide) polyesters which are useful as additives at 0.001% to 0.5% level in triglyceride salad oils to prevent clouding in low-temperature storage of the oils. The degree of esterification is at least 3, i.e., no more than 5 of the 8 hydroxyl groups are unesterified. The ester groups are a combination of: (1) from 15–85% saturated $C_{14}$–$C_{22}$ fatty acids, and (2) the balance selected from saturated $C_2$–$C_{12}$ or unsaturated $C_{14}$–$C_{22}$ fatty acids. Arachidic ($C_{20}$) and behenic ($C_{22}$) acids are recited as specific examples of (1) and acetic ($C_2$), caprylic ($C_8$), and oleic, ($C_{18-1}$) acids are recited as specific examples of (2). At col. 2, lines 5–10, a sucrose ester having 2 oleic and 6 palmitic groups is disclosed, and it is stated that long chain saturated acids such as myristic, stearic, arachidic, behenic, or mixtures thereof can be used in place of all or part of the palmitic.

It is an object of the present invention to provide novel solid nondigestible fat materials which are suitable substitutes for solid fat in foods.

Another object of the present invention is to provide novel, solid, nondigestible fat materials which are especially effective oil binding agents for use in mixture with liquid nondigestible oils in food products to control or prevent passive oil loss of the liquid oils when ingested.

It is another objective of the invention to provide novel solid nondigestible fat materials which are effective in binding oils and are thereby especially useful in formulating shortenings and other semi-solid products and fluid cooking and salad oils from liquid digestible or nondigestible oils.

For purposes of describing this invention, the term "nondigestible" shall mean being absorbable to an extent of only 70% or less (especially 20% or less) by the human body through its digestive system.

All percentages and proportions herein are "by weight" unless otherwise specified.

SUMMARY OF THE INVENTION

The invention is directed to novel solid polyol polyesters wherein the polyol has at least 4 hydroxyl groups, the ester groups comprise a combination of: (i) long chain (at least 12 carbon atoms) unsaturated fatty acid radicals, or a mixture of said radicals and saturated short chain ($C_2$–$C_{12}$) fatty acid radicals, and (ii) long chain (at least 20 carbon atoms) saturated fatty acid radicals, in a molar ratio of (i):(ii) of from about 1:15 to about 2:1, and wherein at least 4 of the hydroxyl groups of the polyol are esterified.

DETAILED DESCRIPTION OF THE INVENTION

It has now been found that certain polyol polyesters which are solid at temperatures of about 25° C. and higher, in addition to being suitable nondigestible substitutes for solid fat in the diet, are highly effective thickening agents for triglyceride oils and nondigestible oils such as liquid polyol polyesters. Accordingly, these solid polyol fatty acid polyesters can be used as "thickening agents" or "hardstocks" for blending with liquid digestible or nondigestible oils in the formulation of cooking and salad oils or semi-solid fat products such as shortenings, as well as other food products which contain a combination of fat and non-fat ingredients, e.g., margarines, mayonnaise, frozen dairy desserts and the like. Further, this high capacity to thicken liquid oils makes compounds of the invention having a melting point above body temperature (37° C.) particularly useful in the formulation of food products containing the nondigestible oils so as to control or prevent the passive oil loss problem associated with the ingestion of such oils.

The novel solid polyol fatty acid polyesters of the present invention are polyol polyesters wherein the ester groups comprise a combination of: (i) long chain, unsaturated fatty acid radicals or a mixture of long chain unsaturated fatty acid radicals and short chain saturated fatty acid radicals, and (ii) long chain saturated fatty acid radicals, the ratio of (i):(ii) being from about 1:15 to about 2:1, and wherein at least about 15% (preferably at least about 30%, more preferably at least about 50%, and most preferably at least about 60%) by weight of the total fatty acid radicals in the solid polyol polyester are $C_{20}$ or higher saturated fatty acid radicals. The long chain unsaturated fatty acid radicals are typically straight chain (i.e., normal) and contain at least about 12 (preferably about 12 to about 26, more preferably about 18 to 22) carbon atoms. The most preferred unsaturated radicals are the $C_{18}$ mono and/or diunsaturated fatty acid radicals. The short chain saturated fatty acid radicals are typically normal and contain 2 to 12 (preferably 6 to 12 and most preferably 8 to 12) carbon atoms. The long chain saturated fatty acid radicals are typically normal and contain at least 20 (preferably 20 to 26, most preferably 22) carbon atoms. The molar ratio of Group (i) fatty acid radicals to Group (ii) fatty acid radicals in the polyester molecule is from about 1:15 to about 2:1 (preferably about 1:7 to about 5:3, more preferably about 1:7 to about 3:5). A typical suitable range is about 3:5 to 4:4. The average degree of esterification of these solid polyol fatty acid polyesters is such that at least 4 of the hydroxyl groups of the polyol are esterified. In the case of sucrose polyesters from about 7 to 8 of the hydroxyl groups of the polyol are preferably esterified. Typically, substantially all (e.g., at least 85%, preferably at least 95%) of the hydroxyl groups of the polyol are esterified.

The polyols which are used in the solid polyol polyester compounds of the present invention preferably contain from about 4 to about 11 (more preferably 4 to 8, most preferably 6 to 8) hydroxyl groups.

Examples of preferred polyols are sugars (including monosaccharides and disaccharides and trisaccharides) and sugar alcohols, containing from 4 to 11 hydroxyl groups. The trisaccharides raffinose and maltotriose are examples of sugars which contain 11 hydroxyl groups. The preferred sugars and sugar alcohols are those which contain 4 to 8 (more preferably 6 to 8) hydroxyl groups. Examples of those containing four hydroxyl groups are the monosaccharides xylose and arabinose and the sugar alcohol erythritol. Suitable five hydroxyl group-containing polyols are the monosaccharides galactose, fructose, mannose and glucose, and the sugar alcohol xylitol. A polyol containing six hydroxyl groups is sorbitol. Examples of disaccharide polyols which can be used include maltose, lactose, and sucrose, all of which contain eight hydroxyl groups.

Examples of other suitable polyols are pentaerythritol, diglycerol, triglycerol, alkyl glycosides, and polyvinyl alcohols. The preferred polyol is sucrose.

Examples of long chain unsaturated fatty acid radicals for the solid polyol polyesters herein are lauroleate, myristoleate, palmitoleate, oleate, elaidate, erucate, linoleate, linolenate, arachidonate, eicosapentaenoate, and docosahexaenoate. For oxidative stability, the mono- and diunsaturated fatty acid radicals are preferred.

Examples of suitable short chain saturated fatty acid radicals are acetate, caproate, caprylate, caprate and laurate.

Examples of suitable long chain saturated fatty acid radicals are arachidate, behenate, lignocerate, and cerotate.

Of course, the long chain unsaturated fatty acid radicals can be used singly or in mixtures with each other or in mixtures with the short chain saturated fatty acid radicals, in all proportions. Likewise, the long chain saturated acid radicals can be used in combination with each other in all proportions. Mixed fatty acid radicals from source oils which contain substantial amounts of the desired unsaturated or saturated acids can be used as the fatty acid radicals to prepare compounds of the invention. The mixed fatty acids from the oils should contain at least about 30% (preferably at least about 50%, and most preferably at least about 80%) of the desired unsaturated or saturated acids. For example, rapeseed oil fatty acids or soybean oil fatty acids can be used instead of pure $C_{12}$–$C_{26}$ unsaturated fatty acids. Hardened (i.e., hydrogenated) high erucic rapeseed oil fatty acids can be used instead of pure $C_{20-26}$ saturated acids. Preferably the $C_{20}$ and higher acids (or their derivatives—e.g., methyl esters) are concentrated, for example by distillation. The fatty acids from palm kernel oil or coconut oil can be used as a source Of $C_8$ to $C_{12}$ acids. An example of the use of source oils to make solid polyol polyesters of the invention is the preparation of solid sucrose polyester, employing the fatty acids of high oleic sunflower oil and substantially completely hydrogenated high erucic rapeseed oil. When sucrose is substantially completely esterified with a 1:3 by weight blend of the methyl esters of the fatty acids of these two oils, the resulting sucrose polyester will have a molar ratio of unsaturated $C_{18}$ acid radicals to $C_{20}$ and higher saturated acid radicals of about 1:1 and 28.6 weight percent of the total fatty acids in the polyester will be $C_{20}$ and $C_{22}$ fatty acids.

The higher the proportions of the desired unsaturated and saturated acids in the fatty acid stocks used in making the solid polyol polyester, the more efficient the ester will be in its ability to bind liquid oils.

The preferred unsaturated fatty acid radicals are those which have 18 carbon atoms, and are mono- and/or lo diunsaturated. Preferred short chain fatty acid radicals are those which have 8–12 carbon atoms. The preferred long chain saturated fatty acid radical is behenate. The preferred ratio of Group (i) fatty acid radicals to Group (ii) fatty acid radicals is from about 1:7 to about 5:3 (more preferably 1:7 to 3:5). Preferred solid polyol polyesters of the invention are polyesters of sucrose in which at least 7 of the 8 hydroxyl groups are esterified.

Examples of solid polyol polyesters of the present invention are sorbitol hexaester in which the acid ester radicals are palmitoleate and arachidate in a 1:2 molar ratio; the octaester of raffinose in which the acid ester radicals are linoleate and behenate in a 1:3 molar ratio; the heptaester of maltose wherein the esterifying acid radicals are sunflower seed oil fatty acids and lignocerate in a 3:4 molar ratio; the octaester of sucrose wherein the esterifying acid radicals are oleate and behenate in a 2:6 molar ratio; and the octaester of sucrose wherein the esterifying acid radicals are laurate, linoleate and behenate in a 1:3:4 molar ratio. A preferred material is sucrose polyester in which the degree of esterification is 7-8, and in which the fatty acid radicals are $C_{18}$ mono- and/or diunsaturated and behenic, in a molar ratio of unsaturates:behenic of 1:7 to 3:5.

The fatty acid composition (FAC) of the polyol polyesters is determined by gas chromatography, using a Hewlett-Packard Model S712A gas chromatograph equipped with a thermal conductivity detector and a Hewlett-Packard Mode 17671A automatic sampler. The chromatographic method used is described in *Official Methods and Recommended Practices of the American Oil Chemists Society*, 3rd Ed., 1984, Procedures 1-$C_e$62 (incorporated herein by reference).

The solid polyol polyesters of the present invention can be made according to prior known methods for preparing polyesters of polyols. Since the sucrose polyesters are the preferred solid polyol polyesters herein, the invention will be exemplified primarily by these materials. One such method of preparation is by reacting the acid chlorides of the fatty acids with sucrose. In this method a mixture of the Group (i) and Group (ii) acid chlorides can be reacted in one step with sucrose, or the Group (i) and Group (ii) acid chlorides can be reacted sequentially with sucrose. Acid anhydrides can be used, instead of acid chlorides. Another preparation method is by the process of reacting methyl esters of the fatty acids with sucrose in the presence of a fatty acid soap and a basic catalyst such as potassium carbonate. See, U.S. Pat. No. 4,797,300, Jandacek et al, issued Jan. 10, 1989, U.S. Pat. No. 3,963,699, Rizzi et al., issued Jun. 15, 1976; U.S. Pat. No. 4,518,772, Volpenhein, issued May 21, 1985; and U.S. Pat. No. 4,517,360, Volpenhein, issued May 14, 1985, and U.S. Ser. No. 417,990, Letton, filed Oct. 6, 1989, all incorporated herein by reference.

When using the methyl ester route for preparing the solid polyol polyesters herein in which the Group (i) fatty acids are the long chain unsaturated acids, the saturated long chain and unsaturated long chain methyl esters are blended in the desired ratio and reacted with sucrose by transesterification to obtain the sucrose esters of mixed unsaturated/saturated fatty acids. In a preferred way of practicing the methyl ester process, five moles of the blended long chain saturated/long chain unsaturated methyl gesters are reacted with sucrose in a first stage at 135° C. to obtain partial esters of sucrose. An additional nine moles of the blended esters are then added and the reaction continued at 135° C. under reduced pressure until the desired degree of esterification has been attained.

The solid polyol polyesters of the present invention have complete melting points above about 25° C., preferably above 37° C., more preferably above about 50° C. and most preferably above about 60° C. Melting points reported herein are measured by Differential Scanning Calorimetry (DSC). These solid materials have the ability to trap relatively large amounts of oil within their crystal structure. As a consequence, they can be used as "hardstocks" by blending them in amounts of about 1% to 50% (typically 1% to 25%) with liquid oils to prepare semi-solid compositions such as shortenings and margarines. A typical suitable range is from 10% to 25%. The oils for these compositions can be conventional digestible triglyceride oils such as cottonseed, corn, canola, or soybean oil, or nondigestible edible oils. The solid polyol polyesters of the invention having complete melting points above 37° C. can be blended at levels of as low as about 1% (preferably at least 2%) with liquid nondigestible oils having complete melting points below 37° C. in order to control passive oil loss upon ingestion of food compositions containing the nondigestible oil.

Examples of nondigestible edible oils which can be used in compositions of the invention are liquid polyesters of sugars and sugar alcohols (U.S. Pat. No. "4,005,195, Jandacek, issued Jan. 25, 1977); liquid esters of tricarballylic acids (U.S. Pat. No. 4,508,746, Hamm, issued Apr. 2, 1985); liquid diesters of dicarboxylic acids such as derivates of malonic and succinic acid (U.S. Pat. No. 4,582,927, Fulcher, issued Apr. 15, 1986); liquid triglycerides of alpha-branched chain carboxylic acids (U.S. Pat. No. 3,579,548, Whyte, issued May 18, 1971); liquid ethers and ether esters containing the neopentyl moiety (U.S. Pat. No. 2,962,419, Minich, issued Nov. 29, 1960; liquid fatty polyethers of polyglycerol (U.S. Pat. No. 3,932,532, Hunter et al., issued Jan. 13, 1976); liquid alkyl glycoside polyesters (U.S. Pat. 4,840,815 to Meyer et al., issued Jun. 20, 1989); liquid polyesters of two ether-linked hydroxycarboxylic acids (e.g., citric or isocitric) (U.S. Pat. 4,888,195 to Huhn et al., issued Dec. 19, 1988); liquid esters of epoxide-extended polyols (U.S. Pat. 4,861,613 to White et al, issued Aug. 29, 1989); all incorporated herein by reference. Edible polydimethyl siloxanes (e.g., Fluid Silicones available from Dow-Corning Corporation) constitute another type of nondigestible oil which can be used in the compositions herein.

The preferred nondigestible oils are the liquid (complete melting point below 37° C., preferably below 25° C.) fatty acid polyesters of sugars or sugar alcohols having at least 4 hydroxyl groups, wherein at least 4 of the hydroxyl groups are esterified. The preferred polyol is sucrose. Examples are the hexa, hepta, and octaesters of sucrose. Examples of esterifying acid groups for these esters are soybean, cottonseed, sunflower seed, coconut, and palm kernel acids (see U.S. Pat. 4,005,195, supra).

The solid polyol polyesters of the present invention can be used in mixtures with other solid polyol polyesters, solid fatty acids or solid triglycerides such as disclosed in U.S. Pat. 4,005,195 (Jandacek), issued Jan. 25, 1977, in order to control oil loss resulting from ingestion of nondigestible liquid polyol polyesters. They can al so be combined with intermediate melting mixtures of liquid and solid nondigestible polyol polyesters such as those disclosed in U.S. Pat. 4,880,657 (Guffey et al.), issued Nov. 14, 1989. Both patents are incorporated by reference herein.

When substituting nondigestible oils for fat in foods which contain fat and non-fat ingredients (e.g., starches, sugar, non-fat milk solids, etc.) the solid polyol polyesters are included to control passive oil loss when said foods are ingested. In such products the mixture of solid polyol polyester of the invention and nondigestible oil is substituted for up to 100% of the fat normally present in such foods. The weight ratio of liquid nondigestible oil to solid polyol polyester will typically be in the range of from about 99:1 to about 1:1, or alternatively from about 99:1 to about 3:1. A typical suitable range is from about 8.9:1 to about 3:1.

The mixtures of solid polyol polyesters of the invention and liquid digestible or nondigestible oils are typically prepared by simply mixing the two materials together, typically at a temperature above the melting point of the solid polyel polyesters.

When using a particularly preferred sucrose polyester of the invention, wherein the unsaturated fatty acid radical is $C_{18}$ mono- and/or diunsaturated and the saturated fatty acid radical is behenic in a molar ratio of 1:7 to 3:5, the preferred ratio of liquid nondigestible oil to solid sucrose polyester is from 99:1 to 9:1, preferably 99:1 to 94:6.

Mixtures of solid polyol polyesters of the invention with edible nondigestible oils are further characterized in having a relatively flat solids content profile across the temperature range of from typical room temperature to body temperature, i.e., from about 21.1° C. (70° F.) to about 37° C. (98.6° F.). The slope of the SFC curve is expressed as the change in percent solids per unit change in temperature, in °F. Typically the slope of the Solid Fat Content (SFC) between these temperatures is between 0 and −0.75. Generally, the greater the weight percent Of $C_{20}$ or higher saturated fatty acid radicals in the solid polyol polyester, the flatter the SFC slope will be. For example, at the 30% $C_{20}$ or higher fatty acid level the slope will typically be between 0 and −0.5 and at 50% it will typically be between 0 and −0.3.

Determination of SFC values over a range of temperatures can be done by a method involving PNMR (Pulsed Nuclear Magnetic Resonance). Such method is well known to those skilled in the art (see *J. Amer. Oil Chem. Soc.*, Vol. 55 (1978), pp. 328-31, and A.O.C.S. Official Method Cd. 16-81, *Official Methods and Recommended Practices of The American Oil Chemists Society*, 3rd. Ed., 1987; both incorporated herein by reference).

Before determining the SFC values, a sample of the fat composition is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; at 32° F. (0° C.) for 15 minutes. After tempering, the SFC values of the sample at temperatures of 50° F. (10° C.), 70° F. (21.1° C.), 80° F. (26.70C), 92° F. (33.3° C.), and 98.60° F. (37° C.) are determined by PNMR after equilibration for 30 minutes at each temperature. The slope of the SFC profile is calculated by subtracting the percent solids at 70° F. from the percent solids at 98.6° F. and dividing that value by 28.6.

The nondigestible solid fat materials herein can be used in combination with other nondigestible or digestible fats and oils to make shortening and oil products. The other fats and oils can be synthetic or derived from animal or vegetable sources, or combinations of these. These shortenings and oils can be used in frying applications such as preparation of french fry potatoes, potato chips, corn chips, tortilla chips, donuts, chicken, fish, and fried pies (e.g., turnovers).

These shortenings and oils can also be used in the production of baked goods in any form, such as mixes, shelf-stable baked goods, and frozen baked goods. Applications include, but are not limited to, cakes, granola bars, brownies, muffins, bar cookies, wafers, biscuits, pastries, pies, pie crusts, and cookies, including sandwich cookies and chocolate chip cookies, particularly the storage-stable dual-textured cookies described in U.S. Pat. No. 4,455,333 of Hong & Brabbs. The baked goods can contain fruit, cream, or other fillings. Other baked good uses include breads and rolls, crackers, pretzels, pancakes, waffles, ice cream cones and cups, yeast-raised baked goods, pizzas and pizza crusts, and baked farinaceous snack foods, and other baked salted snacks.

The solid polyol polyesters herein can also be used as a component of the fat portion of many other foods such as ice cream, frozen desserts, cheese, cheese spreads, meats, meat analogs, chocolate confections, salad dressings, mayonnaise, margarine, spreads, sour cream, yogurt, coffee creamer, peanut butter, extruded snacks, roasted nuts and beverages such as milkshakes.

The present nondigestible solid fat materials can also be fortified with vitamins and minerals, particularly the fat-soluble vitamins. The fat-soluble vitamins include vitamin A, vitamin D, and vitamin E. (See U.S. Pat. No. 4,034,083 (Mattson) issued Jul. 5, 1977, incorporated by reference herein.)

The present nondigestible solid fat materials (or blends thereof with edible oils) are particularly useful in combination with particular classes of food and beverage ingredients. For example, an extra calorie reduction benefit is achieved when the fat materials are used with noncaloric or reduced calorie sweeteners alone or in combination with bulking agents. Noncaloric or reduced calorie sweeteners include, but are not limited to, aspartame, saccharin, alitame, thaumatin, dihydrochalcones, acesulfame, and cyclamates.

The present nondigestible fat materials can also be used in combination with reduced calorie medium chain and mixed medium/long chain triglycerides such as are disclosed in U.S. Pat. No. 4,888,196, Ehrman et al. issued Dec. 19, 1989 and European Patent Application 322,027, Seiden, published Jun. 28, 1989, both incorporated herein by reference.

Bulking or bodying agents are useful in combination with the nondigestible solid fat materials herein in many food compositions. The bulking agents can be nondigestible carbohydrates, for example, polydextrose and cellulose or cellulose derivatives, such as carboxymethylcellulose, carboxyethylcellulose, hydroxypropylcellulose, methylcellulose, hydroxypropyl methylcellulose, and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

Similarly, food and beverage compositions can be made that combine the present nondigestible solid fat materials with dietary fibers to achieve the combined benefits of each. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and manmade fibers (for example, by bacterial synthesis). Commercial fibers such as purified plant cellulose, or cellulose flour, can also be used. Naturally occurring fibers can be used, such as psyllium and fibers from whole citrus peel, citrus albedo, sugar beets, citrus pulp and vesicle solids, apples, apricots, and watermelon rinds.

These dietary fibers may be in a crude or purified form. The dietary fiber used may be of a single type (e.g., cellulose), a composite dietary fiber (e.g., citrus albedo fiber containing cellulose and pectin), or some combination of fibers (e.g., cellulose and a gum). The fibers can be processed by methods known to the art.

Of course, judgment must be exercised to make use of the nondigestible solid fat materials and combinations thereof with other food ingredients. For example, a combination of sweetener and nondigestible solid fat material would not be used where the specific benefits of the two are not desired. The nondigestible solid fat materials and nondigestible solid fat material/ingredient combinations are used where appropriate, and in appropriate amounts.

Many benefits are obtained from the use of the present nondigestible solid fat materials in food and beverage compositions, either when used alone or in combination with edible oils and/or other ingredients discussed above. A primary benefit is the calorie reduction achieved when nondigestible fat materials are used as a total or partial fat replacement. This calorie reduction can be increased by using combinations of the present nondigestible solid fat materials with reduced calorie sweeteners, bulking agents, or other nondigestible fats and oils. Another benefit which follows from this use is a decrease in the total amount of fat and saturated fat in the diet. Foods or beverages made with the nondigestible solid fat materials instead of animal-derived triglyceride fats will also contain less cholesterol, and the ingestion of these foods can lead to reduced serum cholesterol and thus reduced risk of heart disease.

A related benefit is that the use of the nondigestible solid fat materials allows the production of foods that are stable in terms of shelf stability and penetration stability. Compositions made with these fat materials have acceptable organoleptic properties, particularly taste and texture.

Dietary foods can be made with the nondigestible solid fat materials, to meet special dietary needs, for example, of persons who are obese, diabetic, or hypercholesterolemic. The nondigestible solid fat materials can be a major part of a low-fat, low-calorie, low-cholesterol diet, and they can be used alone or in combination with drug therapy or other therapy. Combinations of food or beverage products made with the nondigestible solid fat materials can be used as part of a total dietary management regimen, based on one or more of these products, containing the fat materials alone or in combination with one or more of the above-mentioned ingredients, to provide one or more of the above-mentioned benefits.

In formulating food products comprising fat and nonfat ingredients (e.g., margarines, mayonnaise, baked goods, etc.) in which the fat component comprises a nondigestible oil (e.g., a liquid sucrose polyester such as sucrose octaoleate), the solid polyol polyesters of the present invention can be included in said products to control passive oil loss of the nondigestible oil which would otherwise occur as a result of ingestion of the products. The solid polyol polyester will generally be used in the food products at a level such that the ratio of the nondigestible oil to solid polyol polyester is from about 99:1 to about 1:1, more typically about 99:1 to about 3:1. A typical suitable range is from about 9:1 to about 3:1.

This discussion of the nondigestible solid fat material uses, combinations, and benefits is not intended to be limiting or all-inclusive. It is contemplated that other similar uses and benefits can be found that will fall within the spirit and scope of this invention.

In addition to food compositions, the solid polyol polyesters of the present invention can be used in formulating lubricants, skin creams, cosmetics, pharmaceuticals, and the like.

The invention will be illustrated by the following examples.

EXAMPLE I

Preparation of Tetraoleyl Tetrabehenyl Sucrose (Acid Chloride Route)

| | Chemicals: | Mol. Wt. | Wt. (g) | Moles | Mole Ratio |
|---|---|---|---|---|---|
| A. | Reaction | | | | |
| | 1. Sucrose | 342.3 | 10 | 0.0292 | 1 |
| | 2. Oleyl chloride | 300.47 | 38 | 0.1264 | 4.3 |
| | 3. Behenyl chloride | 358 | 41.8 | 0.1168 | 4 |
| B. | Solvents | | | | |
| | 1. Pyridine | | | | |
| | 2. Dimethylformamide | | | | |
| | 3. Dichloromethane | | | | |

Procedure 10 g of sucrose are dissolved in a solution of 150 ml pyridine and 75 ml dimethylformamide by heating to about 55° C. while under a nitrogen atmosphere. The solution is cooled to about 40° C. and a solution of 41.8 g of behenyl chloride in 150 ml of dichloromethane is added dropwise over a period of 1 hour and 45 minutes. Temperature during the addition is maintained at about 40°-44° C., and the system is also maintained under a nitrogen atmosphere.

Following addition of the behenyl chloride, the reaction is stirred at 40° C. for an additional 3 hours, then cooled to 30° C. 38 g of oleyl chloride in 100 ml of dichloromethane are then added dropwise over a 45 minutes period. The reaction temperature is maintained at about 30° C. during this addition period, then raised to 40° C. and held at that temperature for about 1 hour and 30 minutes. Heat is then discontinued and the reaction mixture stirred at ambient temperature overnight.

The reaction mixture is then warmed to 40° C. and stirred at 40° C. for one hour before cooling to room temperature (about 27° C.). The mixture is then filtered to remove crystalline pyridine hydrochloride and the filtrate is stripped under vacuum to remove dichloromethane, pyridine, and dimethylformamide. The distillation residue is then re-dissolved in dichloromethane and the solution transferred to a 2-liter separatory funnel.

The dichloromethane solution is then washed two times with a dilute solution of sodium chloride, then with a dilute solution of hydrochloric acid to remove residual pyridine. The dichloromethane solution is then washed two times with water, then with dilute calcium hydroxide solution. The dichloromethane/water mixture is then filtered through Celite to remove a small amount of precipitate (probably calcium salts of the acids), then the mixture is separated in a 2-liter separatory funnel. The dichloromethane solution is then washed neutral with water and the dichloromethane solution is dried over magnesium sulfate for several days. The dried mixture is then filtered and stripped under vacuum to give a residue which solidifies at room temperature. The solid polyol polyester has a hydroxyl value of 5.7 (corresponding to a calculated degree of esterification of 7.73—about 93% of hydroxyl groups esterified). The percent octaester in the material is 83.

EXAMPLE II

Preparation of a Solid Sucrose Polyester from Methyl Esters Containing High Proportions of $C_{18}$ Unsaturates and $C_{22}$ Saturates This example describes the preparation of solid sucrose polyesters of this invention by a modification of the process described in U.S. Pat. Nos. 4,518,772, supra, and 4,517,360, supra.

High erucic acid rapeseed oil (HEAR) is blended with low erucic acid rapeseed oil (LEAR) to a composition of 38%. erucic acid. The rapeseed oil blend is mixed with 3%-6% refined, bleached cottonseed oil to obtain an oil composition having approximately 35% of $C_{22}$ acids (i.e., behenic plus erucic). This rapeseed/cottonseed stock is then hydrogenated to an iodine value less than 4. Hydrogenation is done with nickel catalyst levels typical of those used for any vegetable oil using 0–100 psig pressure, and a temperature of approximately 375° F.

The material is deodorized at a temperature of 375°–495° F. The hardened, deodorized rapeseed/cottonseed oil has the following characteristics: fatty acid composition: 3–7% $C_{16:0}$, 45–55% $C_{18:0}$, 0–2% $C_{18:1}$, 0–1% $C_{18:2}$, 4–8% $C_{20:0}$, 33–37% $C_{22:0}$, 0–1% $C_{22:1}$, 0–2% $C_{24:0}$. Free fatty acid content is 0.01–0.1% and Lovibond food color is about 1.0.

The rapeseed/cottonseed oil is converted into methyl esters through an esterification process in which the oil is mixed with methanol, a sodium methoxide catalyst is added, and the reaction is continued until all the triglycerides are converted into methyl esters. Glycerine is settled by gravity after the reaction is completed. The esters are then water washed with hot water to remove trace levels of glycerine and soap. The water phase is settled out by gravity after each wash.

The esters are flash distilled in a batch mode to both remove unsaponifiable materials and to obtain a more concentrated $C_{22}$ material. The distillation is done under a vacuum of 0.5–2mm Hg and a temperature of 300°–410° F. The last 10%–15% of the esters distilled are collected into a clean vessel for use in making the desired sucrose polyester. The other 85–90% is discarded. The ester composition of the last 10–15% collected is: 4% $C_{18:0}$, 6% $C_{20:0}$, 87% $C_{22:0}$, 3% $C_{24:0}$. These are esters "A".

Refined and bleached sunflower oil is deodorized at a temperature of 375°–495° F. under vacuum. The deodorized sunflower oil has the following characteristics: Iodine Value: 125–140; fatty acid composition: 5–10% $C_{16:0}$, 2–6% $C_{18:0}$, 19–26% $C_{18:1}$, 63–74% $C_{18:2}$, 0–2% $C_{18:3}$, 0–1% $C_{20:0}$, 0–1% $C_{22:0}$. Free fatty acid content is 0.01–0.1% and Lovibond red color is about 1.3.

The sunflower oil is converted into methyl esters through the same esterification process as described above. The esters are flash distilled-in a batch mode, primarily to remove unsaponifiable materials. The distillation is done under a vacuum of 0.5–2.0 mm Hg and a temperature of 300°–410° F. These are esters "B".

About 70.5 Kg of methyl esters of refined soybean oil fatty acid, hardened to an IV of about 2, are mixed with 209 Kg of methanol and 15.4 Kg of potassium hydroxide in a stainless steel batch reactor. The mixture is heated to about 145° F. (63° C.) with agitation for 1 to 3 hours at atmospheric pressure. During this time, all but a residual amount of the methyl esters are saponified to make soap.

About 1193.6 Kg of ester "A" is blended with 241.4 Kg of ester "B" to make ester blend "C". The ester composition of blend "C" is about: 1.2% $C_{16:0}$, 3.8% $C_{18:0}$, 3.8% $C_{18:1}$, 10.7% $C_{18:2}$, 4.7% $C_{20:0}$, 71.9% $C_{22:0}$, 3% $C_{24:0}$. About 545.5 Kg. of ester "C" are added to the previously made soap mixture.

About 104.5 Kg of granular sucrose is then added to give a 5:1 molar ratio of methyl ester to sucrose. Potassium carbonate is then added to the mixture (approx. 0.5 wt. percent of the reaction mix) to catalyze the transesterification. This mixture is agitated and slowly heated at atmospheric pressure until the temperature reaches about 275° F. (135° C.). This is to remove the methanol. A vacuum is then pulled and the mixture agitated for up to 8 hours to form the mono-, di- and trisucrose esters. Small quantities of tetra- and pentaesters are also formed during this stage. Additional methyl ester "C" (890 Kg) which has been preheated to 275° F. (135° C.) is added to bring and maintain the molar ratio of the esters to sucrose to 14–15:1. Additional potassium carbonate is then added twice to the mixture (each addition being approximately 0.5 wt. percent of the initial reaction mix). When the reaction conditions stabilize at 275° F. (135° C.), a nitrogen sparge is used to improve agitation and promote methanol stripping. This second reaction stage lasts approximately 4 to,13 hours.

The reaction mixture is then cooled under nitrogen to between 149° F. (65° C.) and 185° F. (85° C.). The crude reaction mixture is agitated with about 91 Kg water. The hydrated crude reaction mixture is passed through a centrifuge to separate a heavy and a light phase. The heavy phase which contains the soaps, excess sugars and potassium carbonate is discarded. The light phase was then washed with an additional 264 Kg of water.

The light phase, which contains methyl esters and the sucrose polyester is then dried to remove moisture at 170° F.–190° F. (76°–88° C.) under 70 mm Hg or less vacuum for 30 to 60 minutes. Filtrol 105 (1.0 wt. percent) is added and the mix is agitated at 167° F. (75° C.) to 190° F. (88° C.). The slurry is separated by filtration or other means until there is less than 0.1 wt. percent fines. The liquid is then passed through a 1 micromillimeter filter.

The refined and bleached reaction mix is then passed through a stainless steel wiped-film evaporator or other suitable equipment to distill off the bulk of the methyl esters. The distillation takes place at 392° F. (200° C.) to 455° F. (235° C.) under approximately 0.5 mm Hg of vacuum.

The sucrose polyester is then deodorized by passing downward through a stainless steel packed column deodorizer or other suitable device at 392° F. (200° C.) to 450° F. (232° C.) under a vacuum of about <25 mm Hg. Steam is introduced to the bottom of the column and passes counter-currently to the sucrose polyester. Feed rates and temperature are adjusted until the methyl ester content of the sucrose polyester is below 1000 ppm. The mixture is then cooled to between 149° F. (65° C.) to 185° F. (85° C.) and passed through a 1 micromillimeter filter. The sucrose polyester is stored in clean stainless steel drums.

Sucrose polyester made according to this procedure has the following approximate composition and properties:

| Fatty Acid Composition | |
|---|---|
| $C_{16}$ | 1.2% |
| $C_{17}$ | 0 |
| $C_{16:1}$ | 0 |
| $C_{18}$ | 4.6 |
| $C_{18:1}$ | 3.7 |
| $C_{18:2}$ | 10.9 |
| $C_{18:3}$ | 0 |
| $C_{20}$ | 4.6 |
| $C_{20:1}$ | 0 |
| $C_{22}$ | 71.7 |
| $C_{22:1}$ | 0.2 |
| $C_{24}$ | 2.8 |
| Other | 0.4 |
| Iodine Value | 22.4 |
| Complete Melting Point (By Differential Scanning Calorimetry) | 70.4° C. |
| Ester Distribution | |
| Octa | 71.6% |
| Hepta | 28.2 |
| Hexa | 0.2 |
| Penta | <0.1 |
| Lower | <0.1 |

By varying the fatty acid composition of ester "A" and/or ester "B", and/or varying the ratio of ester "A" and ester "B" in preparing ester "C", this process can be used to make other solid sucrose polyol polyesters of the invention.

Complete melting point by DSC is determined as follows:

Equipment:
Perkin-Elmer 7 Series Thermal Analysis System, Model DSC7, manufactured by Perkin-Elmer, Norwalk, Conn.

Procedure:
1. Sample is heated to at least 10° C. above the complete melt point and mixed thoroughly.
2. 10±2 mg of sample is weighed into sample pan.
3. A scan is performed from about 10° C. above the complete melt point to −60° C. at 5° C. per minute.
4. The temperature of the sample is maintained at −60° C. for 3 minutes and scanned from −60° C. to the original starting temperature at 5° C. per minute (i.e., about 10° C. above the complete melt point).
5. The complete melt point is the temperature at the intersection of the baseline (specific heat line) with the line tangent to the trailing edge of the endothermic peak.

EXAMPLE III

Preparation of a Shortening from the Solid Polyol Polyester of Example I and a Liquid Sucrose Polyester A noncaloric fat composition suitable for use as a solid shortening is prepared as follows:

Six grams of a solid sucrose polyester prepared according to Example I, and 24 grams of a liquid sucrose polyol ester, in which the sucrose is substantially completely esterified with fatty acid groups of soybean oil which are hydrogenated to an iodine value of about 107, are mixed and heated until all solids are dissolved. The mixture is allowed to cool back to room temperature to form a plastic composition consisting of 20% solid sucrose polyester of Example I and 80% liquid sucrose polyester. The composition is suitable for use as a food fat, and does not produce the anal leakage problem which would otherwise result if only the liquid sucrose polyester is used as a food fat.

The shortening composition can be treated in the conventional manner with air or nitrogen to form an "aerated" shortening.

EXAMPLE IV

Preparation of Shortening from a Solid Polyol Polyester of Example II, Liquid Sucrose Polyester, and Triglycerides A high quality, reduced calorie, plastic shortening especially suitable for household use in cooking/frying applications is prepared according to the following formula.

| Ingredient | % |
|---|---|
| Solid sucrose fatty acid polyester (prepared according to the method of Example II) | 1.05 |
| Liquid digestible oil (soybean oil with an Iodine Value of 107) | 43.10 |
| Intermediate melting fraction triglyceride (cotton/soy oil hydrogenated to an iodine value of 48) | 12.60 |
| Hardstock (cotton stearin hardened to an Iodine Value of 1) | 6.30 |
| Liquid sucrose fatty acid polyester nondigestible oil | 33.95 |
| Emulsifier (mono/diglycerides) | 3.00 |
| | 100.00 |

The above ingredients have the following attributes:

| | Solid Sucrose Polyester % | Liquid Sucrose Polyester % |
|---|---|---|
| Fatty Acid Content | | |
| C12 | — | — |
| C14 | — | — |
| C16 | 1.2 | 9.7 |
| C18 | 4.6 | 5.9 |
| C18:1 | 3.7 | 64.5 |
| C18:2 | 10.9 | 18.9 |
| C18:3 | 0 | 0.2 |
| C17 | 0 | 0.1 |
| C20 | 4.6 | 0.3 |
| C22 | 71.7 | 0.2 |
| C22:1 | 0.2 | 0.2 |
| C24 | 2.8 | — |
| Other | 0.4 | 0.2 |
| Ester Distribution | | |
| Octa | 71.6 | 78.7 |
| Hepta | 28.2 | 21.0 |
| Hexa | 0.2 | 0.2 |
| Lower | <0.2 | 0.3 |

The above ingredients are plasticized by a freeze/pick process, and nitrogen gas is dispersed in the shortening for appearance. The shortening is tempered at 85° F. for 24 hours, then stored at 70° F. (21° C.).

EXAMPLE V

Preparation of Salad Oil from a Solid Polyol Polyester, Liquid Sucrose Polyester, and Triglyceride A substantially clear salad oil is prepared according to the following formula:

| Ingredient | Weight % |
| --- | --- |
| Solid sucrose fatty acid polyester (prepared according to the acid chloride route) | 0.35 |
| Liquid sucrose fatty acid polyester nondigestible oil | 34.65 |
| Liquid triglyceride digestible oil (unhardened canola) | 65.00 |
| | 100.00 |

The sucrose polyesters have the following attributes:

| Fatty Acid Content | Solid Sucrose Polyester % | Liquid Sucrose Polyester % |
| --- | --- | --- |
| C6 | .55 | — |
| C8 | .24 | — |
| C10 | — | — |
| C13 | .04 | — |
| C14 | .04 | — |
| C16 | .84 | 9.1 |
| C17 | 0.5 | 0.1 |
| C18 | 1.3 | 6.4 |
| C18:1 | 16.63 | 64.4 |
| C18:2 | 0.10 | 18.9 |
| C18:3 | — | 0.3 |
| C20 | 4.05 | 0.3 |
| C22 | 74.17 | 0.2 |
| C24 | 0.5 | — |
| Other | 1.05 | 0.2 |

The ingredients are mixed at approximately 80° C. and are then cooled to room temperature. The product is then deaerated to insure no air bubbles are trapped within the product.

EXAMPLE VI

Mayonnaise Composition

A mayonnaise composition of the present invention is made according to the following formula:

| Ingredient | % By Weight |
| --- | --- |
| Egg Yolk | 8.0 |
| Vinegar | 11.0 |
| Sugar | 2.0 |
| Salt | 1.3 |
| Liquid sucrose octaester of partially hydrogenated soybean oil (I.V. 85) | 66.0 |
| Solid sucrose octaester of mixture of fatty acids from high oleic sunflower oil:behenic acid, 4:4 molar ratio | 11.7 |
| | 100.0 |

EXAMPLE VII

Margarine Composition

A margarine composition of the present invention is made according to the following formula:

| Ingredient | % By Weight |
| --- | --- |
| Liquid sucrose octaester of partially hydrogenated (I.V. 85) soybean oil | 68.0 |
| Solid sucrose octaester of mixture of fatty acids from high oleic sunflower oil:behenic acid in 2:6 molar ratio | 12.0 |
| Milk solids | 2.0 |
| Salt | 2.0 |
| Fatty monoglyceride | 1.0 |
| Water | 15.0 |
| | 100.0 |

EXAMPLE VIII

Frying Fat Composition for Potato Chips

A frying fat composition which is particularly suitable for frying potato chips has the following composition:

| Ingredient | Weight % |
| --- | --- |
| Solid sucrose polyester of the invention | 1.8 |
| Liquid sucrose polyester | 58.2 |
| Cottonseed oil | 40.0 |

The solid ester is prepared by esterification of sucrose with (i) high oleic sunflower oil methyl esters and (ii) methyl esters of a mixture of fatty acids containing about 88.5% behenic. The molar ratio of (i) to (ii) is about 2:6. The solid SPE has the following approximate fatty acid composition: $C_{16:0}$ 0.9%; $C_{18:0}$ 1.3%; $C_{18-1}$ 16.7%, $C_{18:2}$ 1.6%; $C_{20:0}$ 4.6% $C_{22:0}$ 72.3%; $C_{24:0}$ 1.9%. Ester content is approximately: octa 82.6%; hepta 17.1%; hexs 0.1%; lower <0.1%. The liquid sucrose polyester is obtained by esterifying sucrose with methyl esters of soybean oil fatty acids, hardened to an iodine value of about 80. The ester content is about 91.9% octa, 8.1% hepta; <0.1% hexa; <0.1% penta; and <0.1% lower.

The composition is prepared by adding the solid sucrose polyester to a mixture of the heated liquid sucrose polyester and cottonseed oil, mixing until the solid has dissolved, and then cooling.

Approximately 225 Norchip potato slices which have a thickness of about 0.052 inches (0.13 cm) are fried in the fat composition in a 5 pound oil capacity batch fryer at a temperature of 365° F. (185° C.) for 3 minutes, 5 seconds. The fried chips have excellent taste and mouthfeel.

EXAMPLE IX

A cooking oil of the present invention is prepared having the following formula:

| Ingredient | Weight % |
| --- | --- |
| Solid sucrose fatty acid polyester (prepared according to the method of Example II) | 1.05 |
| Liquid sucrose fatty acid polyester nondigestible oil | 33.95 |
| Liquid triglyceride digestible oil unhardened canola | 65.00 |
| | 100.00 |

The sucrose polyesters have the following attributes:

|  | Solid Sucrose Polyester | Liquid Sucrose Polyester |
| --- | --- | --- |
| Fatty Acid Content |  |  |
| C10 | — | — |
| C12 | — | — |
| C16 | 1.2 | 10.0 |
| C16-1 | — | 0.1 |
| C18 | 4.6 | 8.0 |
| C18:1 | 3.7 | 69.1 |
| C18:2 | 10.9 | 11.1 |
| C18:3 | 0 | 0.2 |
| C20 | 4.6 | 0.3 |
| C20-1 | — | 0.3 |
| C22 | 71.7 | 0.2 |
| C22:1 | 0.2 | — |
| C24 | 2.8 | — |
| Other | 0.4 | 0.7 |
| Ester Distribution |  |  |
| Octa | 71.6 | 91.0 |
| Hepta | 28.2 | 9.0 |
| Hexa | 0.2 | <.1 |
| Penta | <0.1 | <0.1 |
| Lower | <0.1 | <0.1 |

The ingredients are mixed at approximately 80° C. and then cooled in a scraped wall heat exchanger outlet temperature of about 17° C. (−8.3° C.). The composition is then deaerated to insure no air bubbles are trapped within the composition.

What is claimed is:

1. A polyol fatty acid polyester having a complete melting point above about 25° C. wherein:
   a) the polyol has at least 4 hydroxyl groups,
   b) the ester groups consist essentially of (i) $C_{12}$ or higher unsaturated fatty acid radicals or a mixture of said unsaturated radicals and $C_2$ to $C_{12}$ saturated fatty acid radicals, and (ii) $C_{20}$ or higher saturated fatty acid radicals, the molar ratio of (i):(ii) is from about 3:5 to about 1:1, and
   c) at least 4 of the hydroxyl groups of the polyol are esterified.

2. The polyol fatty acid polyester of claim 1 wherein:
   a) the polyol has from 4 to 8 hydroxyl groups; and
   b) the unsaturated fatty acid radicals of b)(i) have from 12 to 26 carbon atoms, the saturated fatty acid radicals of b)(ii) have from 20 to 26 carbon atoms.

3. The polyol fatty acid polyester of claim 2 wherein the polyol is a sugar or sugar alcohol.

4. The polyol fatty acid ester of claim 3 wherein the sugar or sugar alcohol has from 6 to 8 hydroxyl groups.

5. The polyol fatty acid polyester of claim 4 wherein the polyol is sucrose.

6. The polyol polyester of claim 5 wherein the fatty acid radicals of b)(i) consist essentially of $C_{18}$ mono- and/or diunsaturated fatty acid radicals.

7. The polyol polyester of claim 6 wherein the saturated fatty acid radicals of b)(ii) consist essentially of behenic acid radicals.

8. The polyol fatty acid polyester of any one of claims 1 through 7 wherein the complete melting point of the polyol polyester is above 37° C.

9. A food composition comprising:
   I. a nondigestible edible oil having a complete melting point below 37° C., and
   II. a solid polyol fatty acid polyester having a complete melting point above 37° C., wherein:
      a) the polyol has at least 4 hydroxyl groups,
      b) the ester groups comprise (i) $C_{12}$ or higher unsaturated fatty acid radicals or a mixture of said unsaturated radicals and $C_2$ to $C_{12}$ saturated fatty acid radicals, and (ii) $C_{20}$ or higher saturated fatty acid radicals, the molar ratio of (i):(ii) is from about 1:15 to about 1:1, wherein at least about 15% by weight of the fatty acid radicals in b) are $C_{20}$ or higher saturated fatty acid radicals, and
      c) at least 4 of the hydroxyl groups of the polyol are esterified,
   wherein the weight ratio of I to II is from about 99:1 to about 1:1, and wherein the slope of the SFC profile of the mixture of I and II between 37° C. and 21.1° C. is between 0.0 and −0.75.

10. The food composition of claim 9 wherein in II:
   a) the polyol has from 4 to 8 hydroxyl groups;
   b) the unsaturated fatty acid radicals of b)(i) have from 12 to 26 carbon atoms, the saturated fatty acid radicals of b)(ii) have from 20 to 26 carbon atoms, the molar ratio of (i) to (ii) is from about 1:7 to about 1:1; and wherein at least about 30% by weight of the fatty acid radicals in b) are $C_{20}$ to $C_{26}$ saturated fatty acid radicals.

11. The composition of claim 10 wherein the weight ratio of I to II is from about 99:1 to about 3:1.

12. The food composition of claim 11 wherein at least about 50% by weight of the fatty acid radicals in b) are $C_{20}$ to $C_{26}$ saturated fatty acid radicals.

13. The food composition of claim 12 wherein the molar ratio of (i) to (ii) in b) is about 1:3 and wherein at least about 60% by weight of the fatty acid radicals in b) are $C_{20}$ to $C_{26}$ saturated fatty acid radicals.

14. The food composition of claim 12 wherein the weight ratio of I to II is from about 99:1 to about 9:1.

15. The composition of claim 12 wherein the polyol of the solid polyol polyester is a sugar or sugar alcohol having from 4 to 8 hydroxyl groups.

16. The composition of claim 15 wherein the polyol of the solid polyol polyester is sugar or sugar alcohol having from 6 to 8 hydroxyl groups.

17. The composition of claim 16 wherein the liquid non-digestible oil is a sucrose fatty acid polyester.

18. The composition of any one of claims 9 through 17 wherein the polyol of the solid polyol polyester is sucrose.

19. The composition of claim 18 wherein in b)(i) the fatty acid groups of the solid polyol polyester consist essentially of $C_{18}$ mono- and/or diunsaturated fatty acid radicals.

20. The composition of claim 18 wherein in b)(i) the saturated fatty acid groups of the solid polyol polyester consist essentially of behenic acid radicals.

21. A food composition comprising:
   I. a digestible edible oil having a complete melting point below 37° C., and
   II. a solid polyol fatty acid polyester having a complete melting point above 25° C., wherein:
      a) the polyol has at least 4 hydroxyl groups,
      b) the ester groups comprise (i) $C_{12}$ or higher unsaturated fatty acid radicals or a mixture of said unsaturated radicals and $C_2$ to $C_{12}$ saturated fatty acid radicals, and (ii) $C_{20}$ or higher saturated fatty acid radicals, the molar ratio of (i):(ii) is from about 1:15 to about 1:1, wherein at least about 15% by weight of the fatty acid radicals in b) are $C_{20}$ or higher saturated fatty acid radicals, and c) at least 4 of the hydroxyl groups of the polyol are esterified, wherein the weight ratio of I to II is from about 9:1 to about 1:1.

22. The food composition of claim 21 wherein in I the digestible oil is a triglyceride and in II:
   a) the polyol has from 4 to 8 hydroxyl groups; and
   b) the unsaturated fatty acid radicals of b)(i) have from 12 to 26 carbon atoms, the saturated fatty acid radicals of b)(ii) have from 20 to 26 carbon atoms, the molar ratio of (i) to (ii) is from about 1:7 to about 1:1; and wherein at least about 30% by weight of the fatty acid radicals in b) are $C_{20}$ to $C_{26}$ saturated fatty acid radicals.

23. The composition of claim 22 wherein the weight ratio of I to II is from about 9:1 to about 3:1.

24. The food composition of claim 23 wherein at least about 50% by weight of the fatty acid radicals in b) are $C_{20}$ to $C_{26}$ saturated fatty acid radicals.

25. The food composition of claim 24 wherein the molar ratio of (i) to (ii) in b) is about 1:3 and wherein at least about 60% by weight of the fatty acid radicals in b) $C_{20}$ to $C_{26}$ saturated fatty acid radicals.

26. The composition of claim 24 wherein the polyol of the solid polyol polyester is a sugar or sugar alcohol having from 4 to 8 hydroxyl groups.

27. The composition of claim 26 wherein the polyol of the solid polyol polyester is sugar or sugar alcohol having from 6 to 8 hydroxyl groups.

28. The composition of any one of claims 21 through 27 wherein the polyol of the solid polyol polyester is sucrose.

29. The composition of claim 28 wherein in b)(i) the fatty acid groups of the solid polyol polyester consist essentially of $C_{18}$ mono- and/or diunsaturated fatty acid radicals.

30. The composition of claim 29 wherein in b)(ii) the saturated fatty acid groups of the solid polyol polyester consist essentially of behenic acid radicals.

* * * * *